US012599427B2

(12) United States Patent
Choi

(10) Patent No.: US 12,599,427 B2
(45) Date of Patent: Apr. 14, 2026

(54) SMOG SUCTION STRUCTURE FOR ELECTROSURGICAL HANDPIECE

(71) Applicants:In-Sang Choi, Uiwang-si (KR); Eun A. Choi, Anyang-si (KR); Bo Hwan Choi, Seongnam-si (KR)

(72) Inventor: In-Sang Choi, Anyang-si (KR)

(73) Assignees: In-Sang Choi, Uiwang-si (KR); Eun A. Choi, Anyang-si (KR); Bo Hwan Choi, Seongnam-si (KR)

( * ) Notice: Subject to any disclaimer, the term of this patent is extended or adjusted under 35 U.S.C. 154(b) by 523 days.

(21) Appl. No.: 18/017,228

(22) PCT Filed: Dec. 3, 2020

(86) PCT No.: PCT/KR2020/017520
§ 371 (c)(1),
(2) Date: Jan. 20, 2023

(87) PCT Pub. No.: WO2022/025358
PCT Pub. Date: Feb. 3, 2022

(65) Prior Publication Data
US 2023/0293225 A1 Sep. 21, 2023

(30) Foreign Application Priority Data
Jul. 30, 2020 (KR) ........................ 10-2020-0095073

(51) Int. Cl.
*A61B 18/14* (2006.01)
*A61B 18/00* (2006.01)
(52) U.S. Cl.
CPC ..................... *A61B 18/1402* (2013.01); *A61B 2018/00172* (2013.01); *A61B 2018/1495* (2013.01); *A61B 2218/008* (2013.01)

(58) Field of Classification Search
CPC .......... A61B 18/1402; A61B 2218/008; A61B 17/32; A61B 2018/00166; A61M 1/84
See application file for complete search history.

(56) References Cited

U.S. PATENT DOCUMENTS

| | | | | | |
|---|---|---|---|---|---|
| 5,693,044 A | * | 12/1997 | Cosmescu | ............ | A61B 18/042 606/49 |
| 5,830,214 A | * | 11/1998 | Flom | .................. | A61B 18/1482 604/35 |
| 2009/0062791 A1 | * | 3/2009 | Lee | .................... | A61B 18/1402 606/45 |

(Continued)

FOREIGN PATENT DOCUMENTS

| | | |
|---|---|---|
| KR | 10-1073767 B1 | 10/2011 |
| KR | 10-2015-0113556 A | 10/2015 |

(Continued)

OTHER PUBLICATIONS

Korean Office Action issued on Jan. 26, 2022 in based KR patent application No. 10-2020-0095073 (5 pages in Korean).

*Primary Examiner* — Sean W Collins
(74) *Attorney, Agent, or Firm* — NSIP Law

(57) ABSTRACT

The present invention relates to a suction structure for an electrosurgical handpiece and particularly to a smog suction structure for a handpiece, the smog suction structure being capable of efficiently suctioning and removing smog which obstructs the view of an operating surgeon and has a harmful effect on health.

7 Claims, 8 Drawing Sheets

(56) References Cited

U.S. PATENT DOCUMENTS

| 2017/0020600 A1* | 1/2017 | Lien | A61B 18/1402 |
| 2019/0110832 A1* | 4/2019 | Simonsen | A61B 18/1402 |
| 2020/0093535 A1* | 3/2020 | Manley | A61B 18/14 |

FOREIGN PATENT DOCUMENTS

| KR | 10-2015-0127195 A | 11/2015 |
| KR | 10-1699586 B1 | 1/2017 |
| KR | 10-2020-0055535 A | 5/2020 |
| WO | WO 2014/152874 A2 | 9/2014 |

* cited by examiner

【FIG. 1】
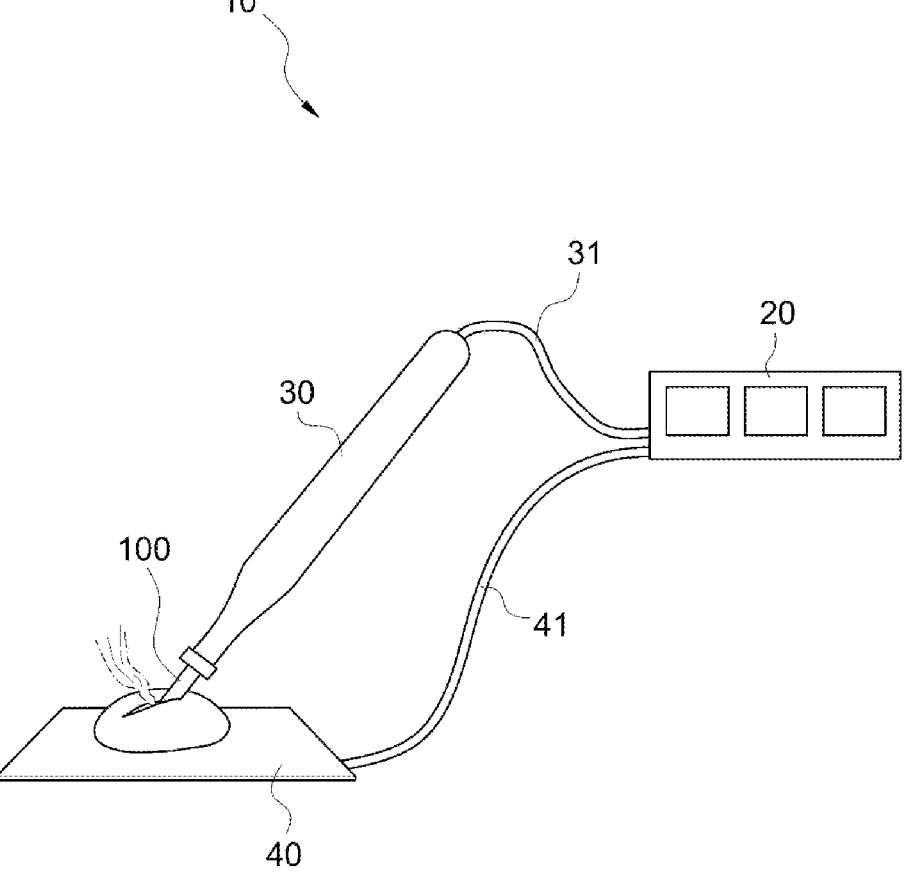

【FIG. 2】
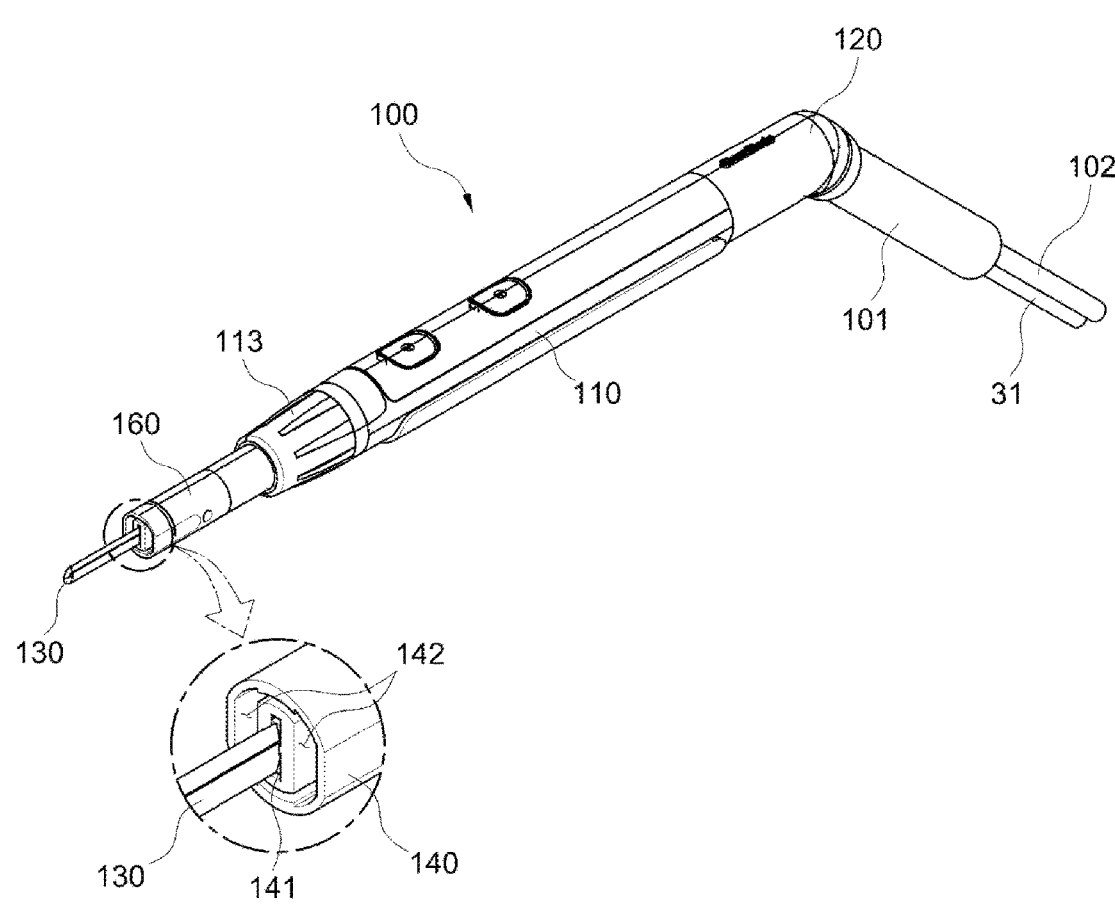

【FIG. 3】
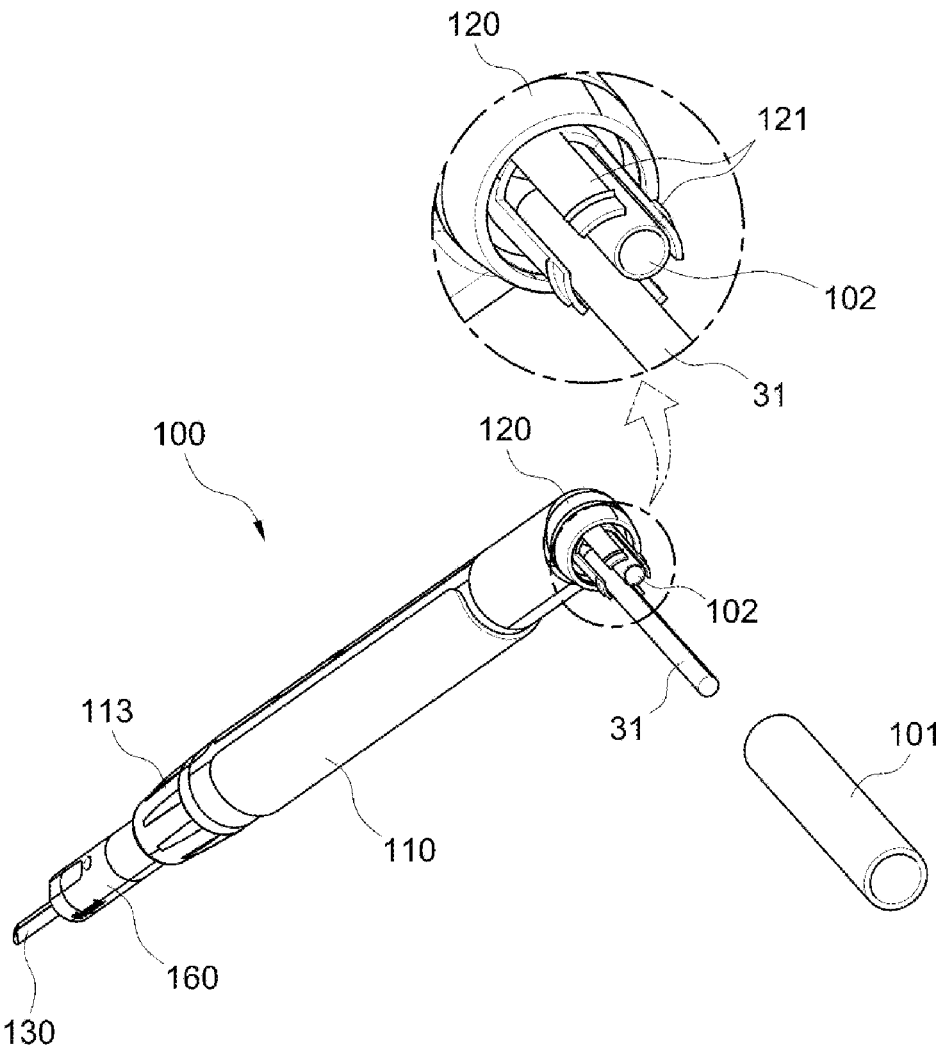

[FIG. 4]
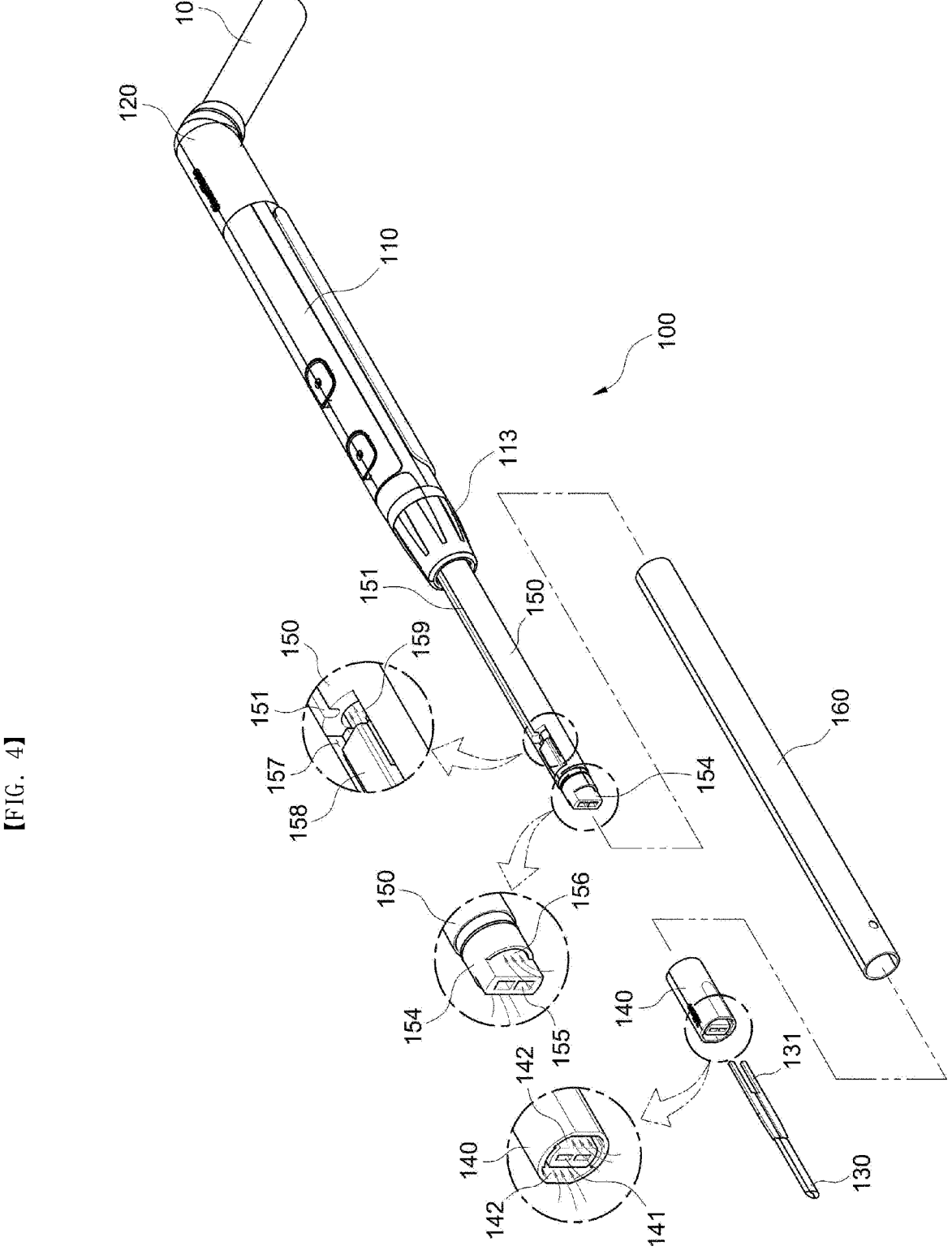

[FIG. 5]
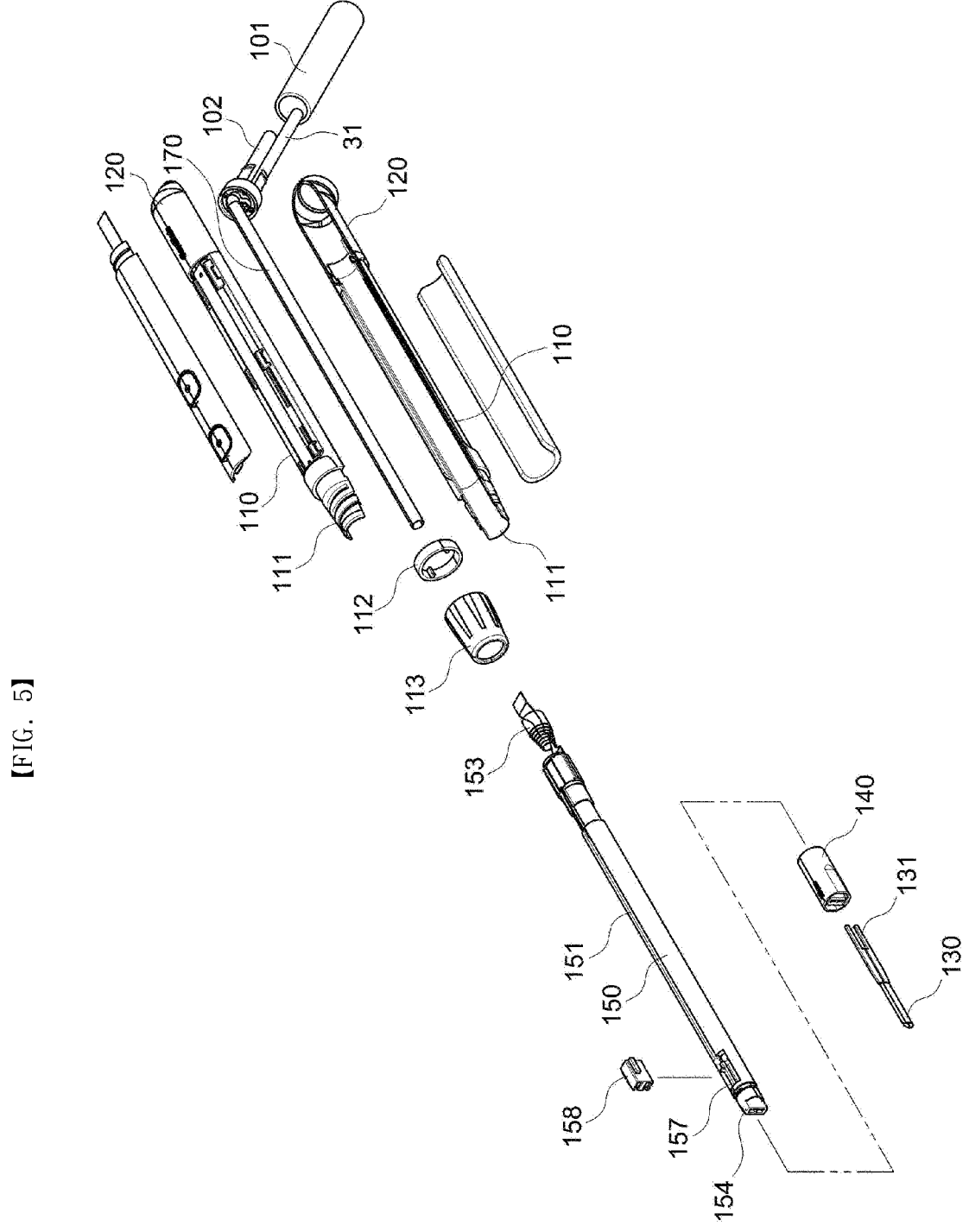

[FIG. 6]
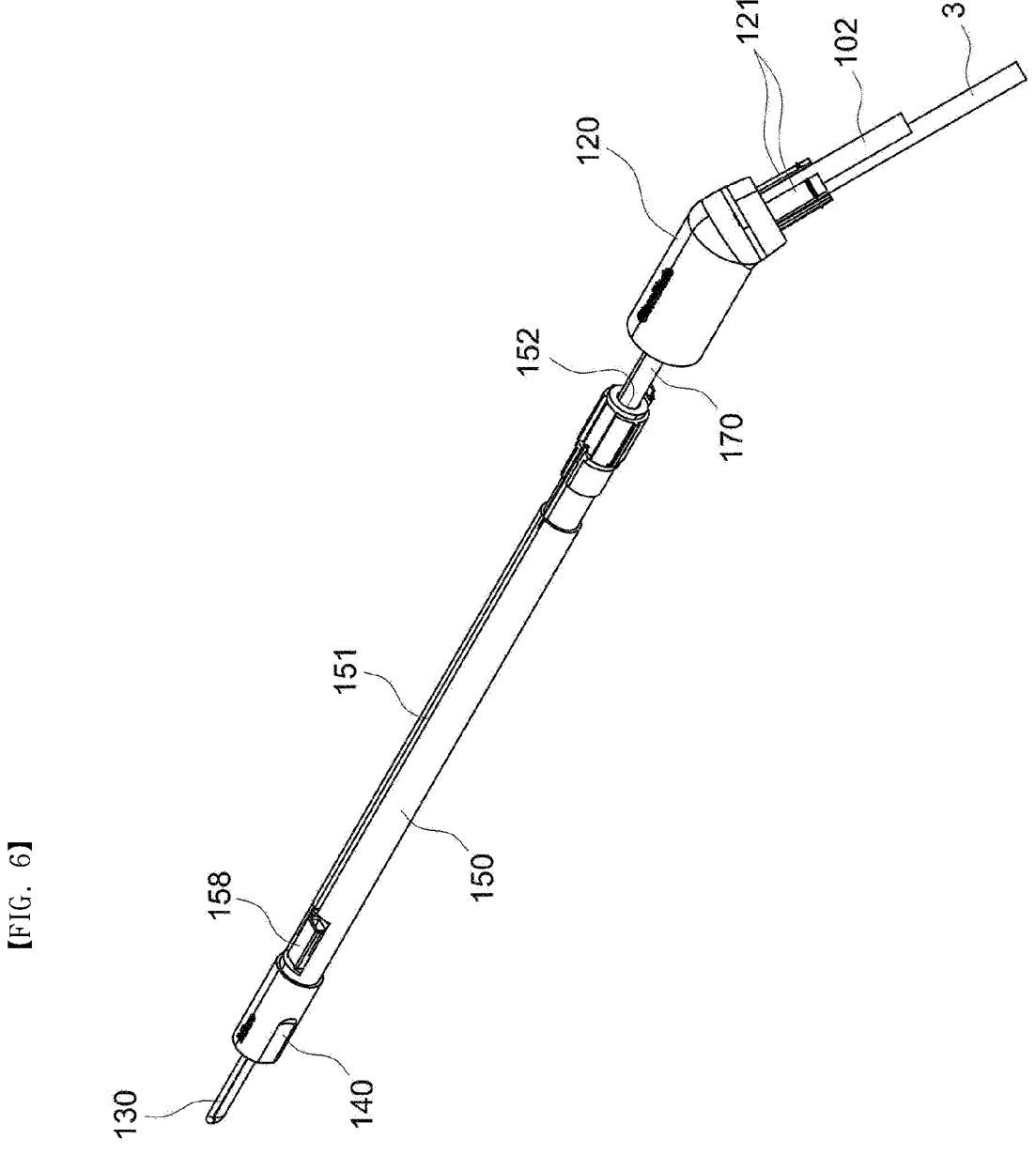

[FIG. 7]
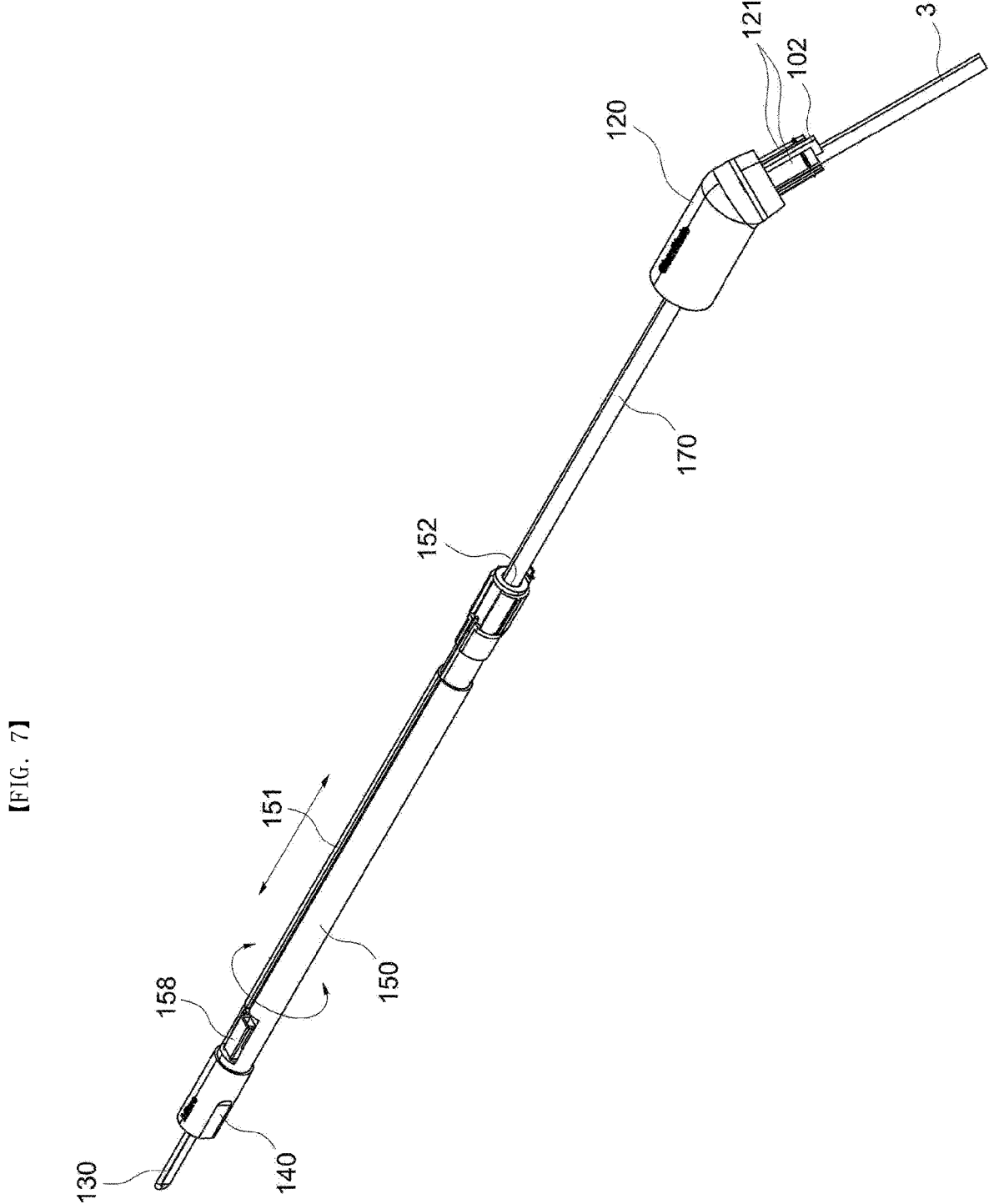

【FIG. 8】
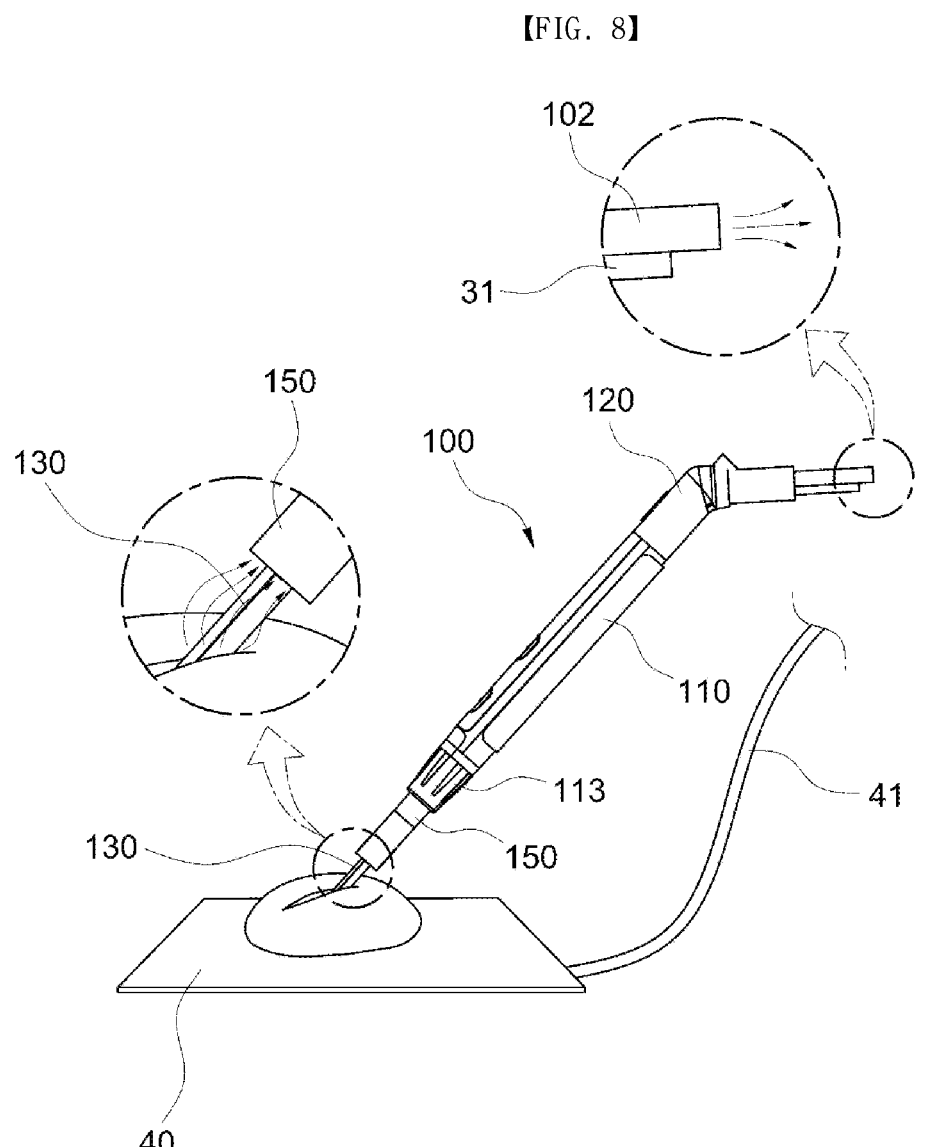

SMOG SUCTION STRUCTURE FOR ELECTROSURGICAL HANDPIECE

CROSS REFERENCE TO RELATED APPLICATIONS

This application is a U.S. National Stage Application of International Application No. PCT/KR2020/017520, filed on Dec. 3, 2020 which claims the benefit under 35 USC 119(a) and 365(b) of Korean Patent Application No. 10-2020-0095073, filed on Jul. 30, 2020 in the Korean Intellectual Property Office, the entire disclosure of which is incorporated herein by reference for all purposes.

TECHNICAL FIELD

The present disclosure relates to a suction structure of an electrosurgical handpiece, and in particular, to a smog suction structure of a handpiece that is capable of efficiently sucking and removing smog that obstructs a surgeon's view and adversely affects health.

BACKGROUND ART

Iron scalpels are widely used in surgical operations, but do not have coagulation effect.

That is, when incising tissue with an iron surgical scalpel, bleeding occurs until the incision is finished or the incised area is naturally coagulated.

Electrosurgery is a surgical method that uses high-frequency (radio frequency) electrical energy to incise, excise, or cauterize a patient's tissue.

Intracellular vibrations are generated by the high-frequency electrical energy supplied through electrodes, and as a result, intracellular temperature is raised and the tissue is heated.

When the intracellular temperature reaches about 60° C., cell death occurs, and when the intracellular temperature increases to 60 to 99° C., the tissue drying (dehydration) and protein coagulation proceeds. When the intracellular temperature reaches 100° C., cell volume expansion and vaporization occur, and tissue is incised or cauterized in this procedure.

In such an electrosurgery, for tissue incision and coagulation, as illustrated in FIG. 1, a controller 20 that generates a high-frequency electric current, and a handpiece 30 that cuts, excises, and cauterizes tissue using the high-frequency electric energy is used. In the incision using an electrosurgical device, heat is generated during the tissue incision procedure by the high-frequency electric current, resulting in a remarkable coagulation effect.

However, electrosurgery incision inevitably causes an arc accompanied by a high temperature since the air insulation layer is destroyed due to incomplete contact between a conductive electrode and the tissue. A burn occurs as the tissue is burned by this arc, and smog is generated as illustrated in FIG. 1 as the tissue is carbonized. It is known that this smog not only obstructs the a surgeon's view, but also adversely affects the health of the surgeon and the patient.

In order to remove the smog generated during the electrosurgical procedure, a handpiece and a separate suction apparatus are used to suction and process the smog. However, there is a problem in that a separate personnel is required to hold the suction device during the surgical procedure.

Recently, a handpiece fastening-type suction apparatus that is fastened to a handpiece to be capable of suctioning smog generated during surgery has been used so that a separate personnel is not required. However, there is a problem in that it is difficult for a surgeon to precisely operate the handpiece as the surgeon is hampered by the suction pipe of the suction apparatus along with the electric cable of the handpiece.

DISCLOSURE OF INVENTION

Technical Problem

The present disclosure has been made to solve the above problems, and provides a smog suction structure of an electrosurgical handpiece that is capable of effectively suctioning and removing smog generated when tissue is incised, excised, or cauterized by using a handpiece.

In addition, the present disclosure provides a smog suction structure of an electrosurgical handpiece that is capable of effectively suctioning and removing smog through a handpiece without using a separate suction apparatus.

Furthermore, the present disclosure provides a smog suction structure of an electrosurgical handpiece that allows a surgeon to perform a precise operation by configuring a suction pipe and electric cable of the handpiece not to hamper a surgeon.

Solution to Problem

In view of the foregoing, an electrosurgical handpiece according to the present disclosure includes: a case 110; a pipe-type inner cylinder 170 inserted into the case 110 and having one side connected to the suction pipe 102 at the rear side of the case 110; a pipe-type operating rod 150 including an inner cylinder insertion hole 152, which is provided at one end so that the inner cylinder 170 is inserted into the inner cylinder insertion hole 152; a connector 154 provided at the other end of the operating rod 150 and including a plug insertion hole 155 and a suction hole 156 configured to suction smog; and a conductive electrode 130, which is inserted into the plug insertion hole 155 to be detachable/attachable.

In this case, the electrosurgical handpiece further includes: a jack seating groove 157 provided in the outer surface of the operating rod 150; a smog inflow hole 159 provided in the jack seating groove 157; and a jack 158 provided with a plug insertion hole into which the plug 131 of the conductive electrode 130 is inserted, and inserted into the jack seating groove 157. Smog suctioned through the suction hole 156 of the connector 154 flows through the jack seating groove 157 and the inflow hole 159.

The electrosurgical handpiece further includes a pipe-type operating rod housing 160 into which the operating rod 150 is inserted to seal the jack seating groove 157.

In addition, a cable 31 configured to supply a current to the conductive electrode 130 and a sheath 101 into which the suction pipe 102 is inserted are fastened to the case 110.

The electrosurgical handpiece further includes a rotator 120 rotatably fastened to the case 110 and configured to prevent twisting of the suction pipe 102 and the cable 31.

The rotator 120 is fastened to the case 110 to be deflected by a predetermined angle from an axial direction of the case 110.

In addition, on the outer surface of the rotator 120, a predetermined number of sheath fixtures 121 on each of which a protrusion protrudes are radially provided so that the sheath 101 is fastened via the sheath fixtures 121 to be detachable/attachable.

Advantageous Effects of Invention

The present disclosure configured described above suctions smog generated when the conductive electrode 130 incises tissue and discharges the smog to the suction pipe 102 connected to the rear side of the handpiece 100. As a result, it is possible for a surgeon to accurately check an affected area with the naked eye and perform surgery, and it is possible to suction and process smog that adversely affects the health of the patient and the surgeon.

In particular, by suctioning smog at a portion closest to the conductive electrode 130 where smog is generated, it is possible to effectively suction and process smog with little escaping smog.

BRIEF DESCRIPTION OF DRAWINGS

FIG. 1 is a view illustrating the configuration of an electrosurgical apparatus.

FIG. 2 is a perspective view illustrating a handpiece according to the present disclosure.

FIG. 3 is a perspective view illustrating a cable configuration of the handpiece according to the present disclosure.

FIGS. 4 and 5 are exploded perspective views illustrating the handpiece according to the present disclosure.

FIGS. 6 and 7 are perspective views illustrating a structure in which a suction pipe is sealed when an operating rod of the handpiece slides.

FIG. 8 is a view illustrating the state of use of the handpiece according to the present disclosure.

DESCRIPTION OF REFERENTIAL NUMERALS OF MAIN PARTS OF DRAWINGS

31: cable
100: handpiece
101: sheath
102: suction pipe
110: case
111: collet
112: fastening ring
113: locking member
120: rotator
121: sheath fixture
130: conductive electrode
131: plug
140: head
141: plug insertion hole
142: suction hole
150: operating rod
151: cable groove
152: inner cylinder insertion hole
153: cable
154: connector
155: plug insertion hole
156: suction hole
157: jack seating groove
158: jack
159: inflow hole
160: operating rod housing

BEST MODE FOR CARRYING OUT THE INVENTION

Hereinafter, the present disclosure will be described in detail with reference to embodiments of the present disclosure and the accompanying drawings, but it will be described on the premise that the same reference numerals refer to the same elements.

In the detailed description of the present disclosure or in the claims, when it is described that one component "comprises" another component, it shall not be limitedly construed as consisting of only the component unless otherwise stated, and shall be understood that other components may be further included.

The terms "upper," "lower," "bottom," "front side," "rear side," "below," etc., used in this specification are merely for facilitating explanation and indicate the orientation of a component as illustrated in the drawings.

In a handpiece 100 according to the present disclosure, as illustrated in FIG. 2, an operating rod 160 is provided in front of a case 110, and a suction pipe 102 and a cable 31 are connected to the rear side of the case 110.

A conductive electrode 130 for incising, excising, and cauterizing tissue is fastened to the tip end of the operating rod 160, and the operating rod 160 is configured to protrude from the case 110 and become longer or to be inserted into the case 110 and become shorter depending on the surgical environment and a surgical site, and the operating rod 160 with an adjusted length is configured to be fixed or released by a locking member 113.

As illustrated in FIG. 4, the conductive electrode 130 is configured such that a plug 131 of the conductive electrode 130 is inserted into a plug insertion hole 141 of a head 140 so as to be replaceable, and the head 140 is configured to be detachable/attachable with respect to the tip end of the operating rod 150.

Suction holes 142 are provided on both lateral sides of the plug insertion hole 141 of the head 140 to suction smog generated during electrosurgery.

A connector 154 is provided at the tip end of the operating rod 150 so that the head 140 is detachable/attachable, and the connector 154 is provided with a plug insertion hole 155 such that the plug 131 of the conductive electrode 130 is inserted into the connector 154. Since the suction holes 156 are provided at both lateral sides of the plug insertion hole 155, the smog suctioned from the suction holes 142 of the head 140 is continuously suctioned through the suction holes 156 of the connector 154.

The operating rod 150 serves to adjust the position of the conductive electrode 130 while protruding from the case 110 of the handpiece 100 or being inserted into the case 110, serves to supply a current to the conductive electrode 130, and serves to cause the smog, which is suctioned from the head 140 and flows through the connector 154, to continuously flow to the rear side of the handpiece 100.

In order to supply the current to the conductive electrode 130, as illustrated in FIG. 4, a cable groove 151 is provided in the form of a groove in the surface of the operating rod 150, and the cable is inserted into the cable groove 151 and fastened to a jack 158 inserted into a jack seating groove 157 in the form a groove provided in the outer surface of the operating rod 150.

A plug groove (not denoted by a reference numeral) is provided in the jack 158, and the plug 131 of the conductive electrode 130 is inserted into the plug groove to supply current to the conductive electrode.

When the jack 158 is inserted into the jack seating groove 157 of the operating rod 150, a space is provided on both the lateral sides and the rear side of the jack 158 as illustrated in FIG. 4, and smog suctioned into the suction holes 156 of the connector 154 and flowing flows into the space on the both lateral sides and the rear side of the jack 158 and is sucked into the inflow hole 159 of the operating rod 150.

In order to hermetically block the smog flowing through the open jack seating groove 157 as described above, the operating rod 150 is inserted into a cylindrical operating rod housing 160 as illustrated in FIG. 4.

As illustrated in FIG. 3, the cable 31 is inserted into the sheath 101 together with the suction pipe 102. The suction pipe 102 is a pipe through which suctioned smog is discharged, and the cable 31 is an electric cable configured to supply a current to the conductive electrode 130.

In this case, by radially configuring sheath fixtures 121, each of which has a protrusion provided on the outer surface thereof at the end of the rotator 120 or the case 110, the sheath 101 may be configured to be easily detachable/attachable via the sheath fixtures 121.

The smog suctioned into the inflow hole 159 provided in the jack seating groove 157 of the operating rod 150 described above flows through the case 110 of the handpiece 100 and is discharged through the suction pipe 102. As described above, the operating rod 150 is configured such that protrusion, insertion, and rotation with respect to the case 110 are enabled. It is necessary to maintain airtightness so that smog does not escape in the process of protrusion, insertion, and rotation of the operating rod 150.

In order to maintain such airtightness for smog, as illustrated in FIG. 5, the inner cylinder 170 connected to the suction pipe 102 is provided inside the case 110, and the inner cylinder 170 is inserted into the inner cylinder insertion hole 152 provided at the rear end of the operating rod 150 as illustrated in FIG. 5.

As described above, when the inner cylinder 170 inside the case 110 is inserted into the inner cylinder insertion hole 152 of the operating rod 150, even if the operating rod 150 slides or rotates as illustrated in FIG. 7, the smog flowing through the operating rod 150 flows into the inner cylinder 170 while maintaining airtightness.

As described above, the operating rod 150 also serves to supply a current to the conductive electrode 130. A cable 153 is installed as illustrated in FIG. 5 to be capable of supplying the current to the conductive electrode 130 even if the operating rod 150 slides or rotates.

By shaping the cable 153 in the form of a rolled thin film, even when the operating rod 150 slides or rotates, the cable 153 is elastically deformed and elastically restored and continuously supplies the current to the conductive electrode 130.

The smog flowing into the inner cylinder 170 is discharged to the suction pipe 102 at the rear end of the handpiece 100 as illustrated in FIG. 8 and processed.

As illustrated in FIG. 3, the cable 31 and the suction pipe 102 are inserted into the sheath 101 at the rear side of the handpiece 100. However, since two pipes are connected to the rear side of the handpiece 100, it becomes difficult for a surgeon to precisely handle the handpiece 100 when performing surgery.

In particular, when a surgeon rotates the handpiece 100 according to a surgical site, the suction pipe 102 and the cable 31 are twisted, making it difficult for the surgeon to precisely handle the handpiece 100.

In order to solve this problem, it is desirable to configure the handpiece 100 to be handled by a surgeon with little force by fastening the suction pipe 102 and the cable 31 so as to be deflected by a predetermined angle from the longitudinal axis of the handpiece 100 and providing the rotator 120 in the portion in which the suction pipe 102 and the cable 31 are fastened to the handpiece 100, as illustrated in FIG. 2.

The rotator 120 is fastened to be rotatable with respect to the case 110 of the handpiece 100, so that when a surgeon grips the handpiece 100 for handling, especially when a surgeon rotates the handpiece, the rotator 120 maintains the suction pipe 102 and the cable 31 to be untwisted while rotating.

The present disclosure configured described above suctions smog generated when the conductive electrode 130 incises tissue and discharges the smog to the suction pipe 102 connected to the rear side of the handpiece 100, as illustrated in FIG. 8. As a result, it is possible for a surgeon to accurately check an affected area with the naked eye and perform surgery, and it is possible to suction and process smog that adversely affects the health of the patient and the surgeon.

In particular, by suctioning smog at the head 140 closest to the conductive electrode 130 where smog is generated, it is possible to effectively suction and process smog with little escaping smog.

In the embodiment of the present disclosure, it has been described that the head 140 is fastened to the connector 154 and the conductive electrode 130 is fastened to the head 140 for easy replacement and rotation of the conductive electrode 130. However, without the configuration of the head 140, the conductive electrode 130 may be configured to be directly inserted and fastened into the plug insertion hole 155 of the connector 154, and the suction holes 156 of the connector 154 may be configured to directly suction the smog generated during surgery.

In the foregoing, the technical idea of the present disclosure has been examined with the above-described embodiments.

It is apparent that a person ordinarily skilled in the art to which the present disclosure belongs can variously modify or change the above-described embodiments based on the description of the present disclosure.

In addition, it is evident that, even if not explicitly shown or described, a person ordinarily skilled in the art to which the present disclosure belongs can make various modifications including the technical idea according to the present disclosure based on the description of the present disclosure, and the modifications still fall into the scope of the present disclosure.

The embodiments described above with reference to the accompanying drawings have been described for the purpose of describing the present disclosure, and the scope of the present disclosure is not limited to these embodiments.

The invention claimed is:

1. A smog suction structure of an electrosurgical handpiece, the smog structure comprising:
   a case (110);
   a pipe-type inner cylinder (170) inserted into the case (110) and having one side connected to a suction pipe (102) at a rear side of the case (110);
   a pipe-type operating rod (150) comprising an inner cylinder insertion hole (152), which is provided at one end so that the inner cylinder (170) is inserted into the inner cylinder insertion hole (152);

a connector (154) provided at another end of the operating rod (150) and comprising a plug insertion hole (155) and a suction hole (156) configured to suction smog; and a conductive electrode (130), which is inserted into the plug insertion hole (155) to be detachable/attachable, wherein the smog suction structure is configured such that the smog suctioned into the suction hole (156) does not come into contact with an inner surface of the case (110) and flows inside the operating rod (150) and the inner cylinder (170) so as to be discharged to the suction pipe (102).

2. The smog suction structure of claim 1, further comprising:

a jack seating groove (157) provided in an outer surface of the operating rod (150);

a smog inflow hole (159) provided in the jack seating groove (157); and a jack (158) provided with a plug insertion hole into which a plug (131) of the conductive electrode (130) is inserted, and inserted into the jack seating groove (157), wherein smog suctioned through the suction hole (156) of the connector (154) flows through the jack seating groove (157) and the inflow hole (159).

3. The smog suction structure of claim 2, further comprising:

a pipe-type operating rod housing (160) into which the operating rod (150) is inserted to seal the jack seating groove (157).

4. The smog suction structure of claim 1, wherein a cable (31) configured to supply a current to the conductive electrode (130) and a sheath (101) into which the suction pipe (102) is inserted are fastened to the case (110).

5. The smog suction structure of claim 4, further comprising:

a rotator (120) rotatably fastened to the case (110) and configured to prevent twisting of the suction pipe (102) and the cable (31).

6. The smog suction structure of claim 5, wherein the rotator (120) is fastened to the case (110) to be deflected by a predetermined angle from an axial direction of the case (110).

7. The smog suction structure of claim 5, wherein, on an outer surface of the rotator (120), a predetermined number of sheath fixtures (121) on each of which a protrusion protrudes are radially provided so that a sheath (101) is fastened via the sheath fixtures (121) to be detachable/attachable.

* * * * *